US012773143B2

(12) United States Patent
Matic et al.

(10) Patent No.: US 12,773,143 B2
(45) Date of Patent: Oct. 27, 2026

(54) METHOD FOR IMPROVING THE SUCCESS OF IMMEDIATE WELLBEING INTERVENTIONS TO ACHIEVE A DESIRED EMOTIONAL STATE

(71) Applicant: KOA HEALTH DIGITAL SOLUTIONS S.L.U., Barcelona (ES)

(72) Inventors: Aleksandar Matic, Lloret de Mar (ES); Jesus Alberto Omaña Iglesias, Barcelona (ES); Amanda J. Henwood, London (GB)

(73) Assignee: KOA HEALTH DIGITAL SOLUTIONS S.L.U., Barcelona (ES)

( * ) Notice: Subject to any disclaimer, the term of this patent is extended or adjusted under 35 U.S.C. 154(b) by 299 days.

(21) Appl. No.: 17/501,511

(22) Filed: Oct. 14, 2021

(65) Prior Publication Data

US 2023/0120262 A1 Apr. 20, 2023

(51) Int. Cl.

| | |
|---|---|
| ***A61B 5/16*** | (2006.01) |
| ***A61B 5/00*** | (2006.01) |
| ***A61B 5/0205*** | (2006.01) |
| ***A61B 5/024*** | (2006.01) |
| ***G06F 3/01*** | (2006.01) |

(52) U.S. Cl.

CPC ............ *A61B 5/165* (2013.01); *A61B 5/0205* (2013.01); *A61B 5/02405* (2013.01); *A61B 5/02416* (2013.01); *A61B 5/681* (2013.01); *G06F 3/015* (2013.01)

(58) Field of Classification Search

CPC ..... A61B 5/64; A61B 5/0205; A61B 5/02405; A61B 5/02416; A61B 5/681; G06F 3/015

USPC ........................................... 600/301; 434/236

See application file for complete search history.

(56) References Cited

U.S. PATENT DOCUMENTS 9,498,704 B1 * 11/2016 Cohen ...................... A63F 13/67
10,799,149 B2 * 10/2020 Freeman ............ A61B 5/02055
10,813,584 B2 * 10/2020 Ben-Kiki ................ G10L 25/63
2003/0009078 A1 * 1/2003 Fedorovskaya .... A61B 5/02055 600/26

(Continued)

FOREIGN PATENT DOCUMENTS

CA 2935813 A1 * 7/2014 ............. G16H 20/70
WO WO-2020018990 A1 * 1/2020 ......... A61H 23/0245

*Primary Examiner* — Michael J Lau

(74) *Attorney, Agent, or Firm* — MARSHALL, GERSTEIN & BORUN LLP

(57) ABSTRACT

A method for recommending those interventions most likely to achieve a desired state involves predicting the efficacy and engagement of interventions based on the experience of prior users who undertook the interventions. Physiological and personal parameters of the user are acquired. The user's initial state and desired state are determined. The engagement and efficacy levels of each intervention are predicted and used to determine the likelihood that the transition achieved by each intervention achieves its predicted end state. The likelihood that a second transition achieves the desired state is also determined based on efficacy and engagement for the second transition whose starting state is the end state of the first transition. The first and second interventions are identified whose associated transitions have the greatest combined likelihood of achieving the desired state compared to all other intervention combinations. The user is then prompted to engage in the first and second interventions.

16 Claims, 6 Drawing Sheets

(56) References Cited

U.S. PATENT DOCUMENTS

| | | | | |
|---|---|---|---|---|
| 2003/0059750 | A1* | 3/2003 | Bindler | G06Q 10/10 434/236 |
| 2011/0183305 | A1* | 7/2011 | Orbach | G09B 19/00 434/236 |
| 2011/0300847 | A1* | 12/2011 | Quy | H04W 4/00 455/419 |
| 2012/0143022 | A1* | 6/2012 | Lee | A61B 5/0295 600/549 |
| 2015/0099987 | A1* | 4/2015 | Bhatkar | A61B 5/02405 600/479 |
| 2016/0005320 | A1* | 1/2016 | deCharms | G09B 19/00 434/236 |
| 2018/0001184 | A1* | 1/2018 | Tran | G16H 50/20 |
| 2018/0012009 | A1* | 1/2018 | Furman | G06F 21/32 |
| 2019/0332902 | A1* | 10/2019 | Gallagher | G06V 10/811 |
| 2020/0008725 | A1* | 1/2020 | Bach | A61B 5/055 |

* cited by examiner

| | PERSONAL CHARACTERISTICS | | | PHYSIOLOGICAL PARAMETERS | | INITIAL STATE | | ACHIEVED STATE | | | |
|---|---|---|---|---|---|---|---|---|---|---|---|
| INTERVENTION | AGE | GENDER | PERSONALITY | AVG HRV | AVG EDA | START HRV | START EDA | END HRV | END EDA | EFFICACY | ENGAGEMENT |
| (0, 1, 0, 0, 0, 0, 0, 0) | 23 | 1 | 34, 49, 23, 33, 44 | 78 | 14 | 50 | 10 | 50 | 3 | 0.93 | 0.75 |
| (0, 0, 0, 1, 0, 0, 0, 0) | 23 | 1 | 34, 49, 23, 33, 44 | 78 | 14 | 34 | 15 | 30 | 20 | 0.12 | 0.22 |
| (0, 0, 0, 1, 0, 0, 0, 0) | 51 | 0 | 43, 21, 20, 39, 39 | 40 | 11 | 39 | 10 | 45 | 5 | 0.99 | 1 |
| ... | ... | ... | ... | ... | ... | ... | ... | ... | ... | ... | ... |

FIG. 7

METHOD FOR IMPROVING THE SUCCESS OF IMMEDIATE WELLBEING INTERVENTIONS TO ACHIEVE A DESIRED EMOTIONAL STATE

TECHNICAL FIELD

The present invention relates to the field of personalized wellbeing interventions that have an immediate impact and more specifically to a method for achieving a desired emotional state of a user of a mobile app.

BACKGROUND

Mobile applications (apps) directed to improving mental health have become more commonly used as a result of the near ubiquity of smartphones. The mobile apps allow mental wellbeing interventions to be delivered in a scalable and cost-effective manner, anytime and anywhere. A wide variety of personalized wellbeing interventions are now available, from meditation and mindfulness to programs covering psychotherapy, such as cognitive behavioral therapy (CBT). Many of the interventions are designed to achieve an immediate (also called momentary) impact on the user's mental state. The momentary interventions promote a positive change in the immediate emotional or cognitive state of the user. For example, meditation apps typically guide users to achieve calm and relaxed states. However, the success of an immediate intervention is directly impacted by how the user feels in the moment, which is influenced by two factors: engagement and efficacy. Engagement signifies the degree to which the user is motivated to engage with a particular intervention. Efficacy indicates how efficacious the intervention is at transitioning the user from the user's initial emotional state to the user's desired emotional state.

Emotional states are affective states that reflect the extent to which people have achieved their goals. Negative emotions, in particular, tend to signal a discrepancy between a person's current emotional state and the person's desired emotional state. Not all negative emotions are the same, however, and the differences determine which kinds of interventions will be successful. Some negative emotions, such as anxiety, can be overcome by engaging in behavior associated with a calming outcome, such as relaxation. Other negative emotions, such as sadness, can be overcome by engaging in behavior that induces happiness, such as practicing gratitude. The close relationship between emotions and motivation plays an important role in determining whether an intervention treatment will be successful.

Therefore, if a user of an immediate intervention app is angry or sad, calming interventions may be less engaging and less efficacious than happiness inducing interventions, which are more closely aligned with the user's desired emotional state (a state with reduced sadness). Particular transitions from a user's initial emotional state to the desired emotional state are more engaging and efficacious than others, and the most successful interventions can be identified in part based on the initial emotional state. Likely successful interventions are also identified based on other factors related to emotion, such as the user's personality and the user's global wellbeing, which are used to predict the user's engagement with the intervention and the efficacy of the intervention.

For example, extraversion is associated with low emotional arousal levels and may therefore result in a desire for more emotionally arousing interventions. Personality types can also predispose people to engage in different types of emotion regulation and can influence the success of the intervention. The success of the intervention therefore depends on the user's initial emotional state, the user's personal characteristics and the available interventions.

Thus, a method is sought for improving the success of immediate wellbeing interventions at achieving a user's desired emotional state.

SUMMARY

A method for recommending wellbeing interventions that are most likely to achieve the user's desired emotional state involves predicting the efficacy and engagement of interventions that are available to the user based on the experience of prior users who undertook those interventions. Physiological parameters and personal characteristics of the user are acquired. The user's initial state and desired state are determined. The engagement level and efficacy level of each available intervention is predicted and used to determine the likelihood that the transition achieved by the associated intervention will achieve its predicted end state. The likelihood that a second transition will achieve the desired state is determined based on the efficacy and engagement associated with the second transition whose starting state is the end state of the first transition. First and second interventions are identified whose associated transitions have the greatest combined likelihood, compared to all other combinations of available interventions, of achieving the desired state by transitioning the user from the initial state through an intermediary state to the desired state. The user is then prompted to engage in the first intervention and then to engage in the second intervention.

In another embodiment, a method for achieving a user's desired emotional state involves determining the weights of transitions achievable by the interventions available to the user of a mobile app. Data concerning physiological parameters of the user and personal characteristics of the user are acquired. The initial emotional state of the user is determined based on the physiological parameters and personal characteristics. The desired emotional state of the user is determined. A set of interventions that can potentially be undertaken by the user are identified.

A computing system associated with the mobile app predicts a first efficacy level of a first intervention of the set of interventions for achieving an intermediary state starting from the initial emotional state of the user. The computing system uses machine learning to predict the efficacy level based on known efficacies of the first intervention undertaken by other users who have personal characteristics similar to those of the user and who sought to achieve states similar to the intermediary state starting from states similar to the initial emotional state. A first engagement level of the user to undertake the first intervention is predicted by using machine learning based on known engagements of others who have undertaken the first intervention and who have personal characteristics similar to those of the user and who sought to achieve states similar to the intermediary state starting from states similar to the initial emotional state. A first weight of a first transition from the initial emotional state to the intermediary state is determined. The first weight indicates a likelihood of success that the user will achieve the intermediary state based on the predicted first efficacy level and on the predicted first engagement level.

The computing system also predicts a second efficacy level of a second intervention from the set of interventions for achieving a target state starting from the intermediary state of the user by using machine learning based on known efficacies of the second intervention undertaken by other users who have personal characteristics similar to those of the user and who sought to achieve states similar to the target state starting from states similar to the intermediary state. The target state approaches the desired emotional state by coming within a predetermined margin of error for valence and arousal of the desired state. A second engagement level of the user to undertake the second intervention is predicted by using machine learning based on known engagements of others who have undertaken the second intervention and who have personal characteristics similar to those of the user and who sought to achieve states similar to the target state starting from states similar to the intermediary state. A second weight of a second transition from the intermediary state to the target state it determined. The second weight indicates the likelihood of success that the user will achieve the target state based on the predicted second efficacy level and on the predicted second engagement level.

A recommended path of transitions from the initial emotional state to the target state is identified. The recommended path of transitions includes the first transition and the second transition. The sum of the first weight and the second weight is smaller than sums of weights of all other paths of transitions from the initial emotional state to the target state. The other paths of transitions correspond to other interventions from the set of interventions. The smaller sum of the first weight and the second weight indicates that the user has a greater likelihood of approaching the desired emotional state by undertaking the first intervention and the second intervention than by undertaking other interventions from the set of interventions that result in other paths of transitions. The mobile app then prompts the user to engage in the first intervention and then to engage in the second intervention.

Other embodiments and advantages are described in the detailed description below. This summary does not purport to define the invention. The invention is defined by the claims.

BRIEF DESCRIPTION OF THE DRAWINGS

The accompanying drawings, where like numerals indicate like components, illustrate embodiments of the invention.

FIG. 7 is a table of database entries showing physiological parameters and personal characteristics associated with particular interventions undertaken by prior users.

DETAILED DESCRIPTION

Reference will now be made in detail to some embodiments of the invention, examples of which are illustrated in the accompanying drawings.

A novel method that optimizes the delivery of immediate wellbeing interventions allows a user of a mobile app to achieve a desired emotional or cognitive state (hereinafter an emotional state) by transitioning to states of calm, relaxation, happiness and focus from states of stress, anxiety and sadness. Based on the user's initial emotional state, the user's personal characteristics and physiological parameters, the method determines both (a) the likelihood that the user will engage with a specific intervention, and (b) the likelihood that the specific intervention will be efficacious in achieving the user's desired emotional state. For a set of available interventions, the method determines a path of transitions resulting from a sequence of associated interventions that are more likely to induce the desired emotional state in the user.

Figure 1:
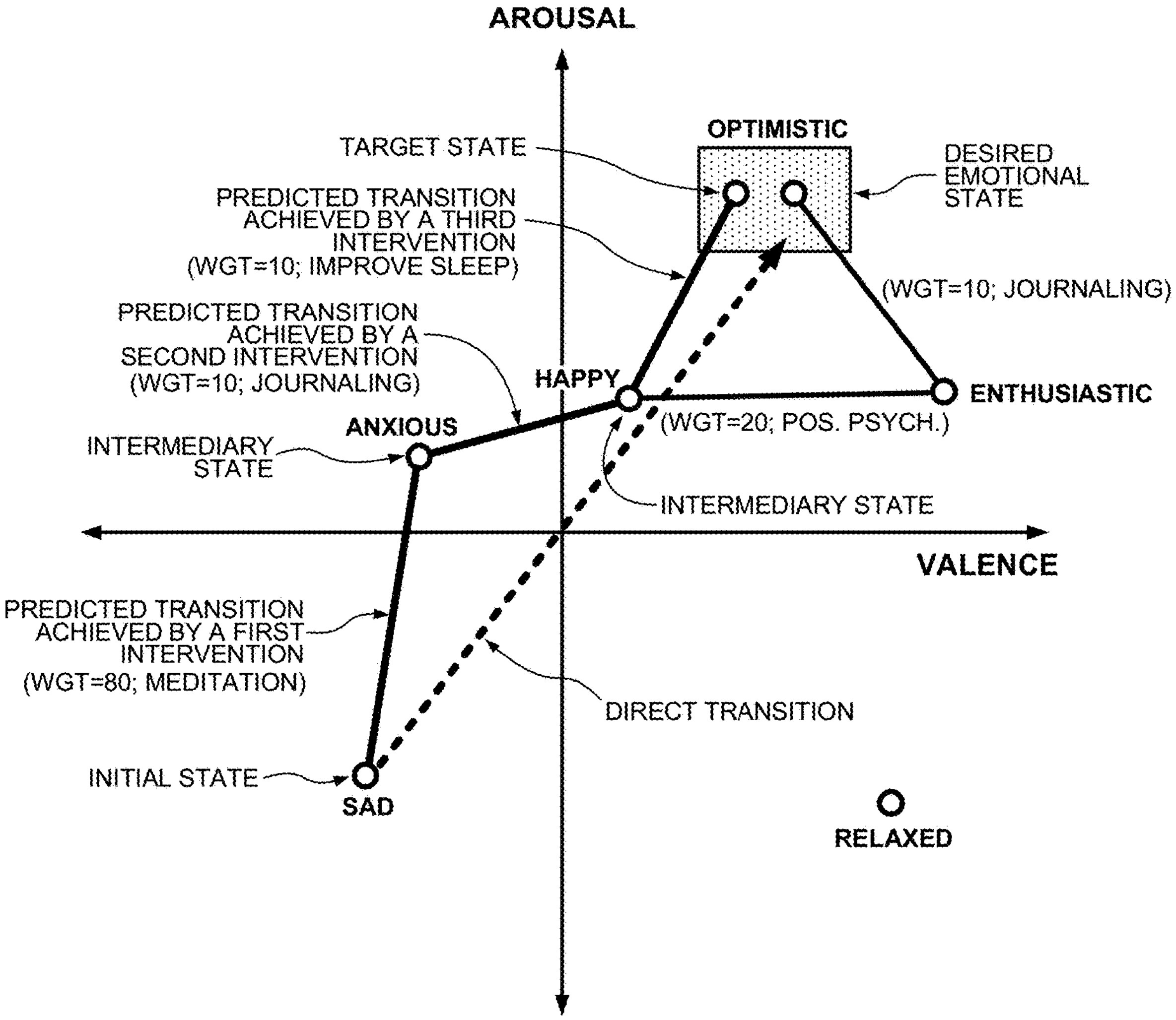
FIG. 1 is a diagram of a valence-arousal coordinate space of emotional states between which a user of a novel smartphone app can transition.

FIG. 1 is a diagram illustrating a valence-arousal coordinate space of emotional states between which the novel method enables the user to transition. The four quadrants of the valence-arousal space correspond loosely to the emotional states "happy" (high valence, high arousal), "relaxed" (high valence, low arousal), "anxious" (low valence, high arousal) and "sad" (low valence, low arousal). The method determines the weight of a direct transition from the initial emotional state of the user to the desired emotional state of the user. The method also determines the weights of multiple sequential transitions that indirectly move the user from the initial state through one or more intermediary states to the desired state.

The indirect transitions form a path from the initial state to a targeted state through one or more intermediary states. The targeted state does not always reach the desired state. The states can be described either as labeled emotional states or only as valence-arousal coordinate pairs. The weight of a transition corresponds to the expected success of an intervention at transitioning the user from one state to another, considering the combined likelihood that the user will engage with the intervention and the likelihood that the intervention will induce the targeted state in the user (i.e., the efficacy of the intervention).

In one embodiment, larger weights are assigned to less probable transitions. In other embodiments, smaller weights represent less probable transitions. A prediction model used by the mobile app is run for all the available interventions to predict the engagement and efficacy of each intervention. The prediction model is run for a set of direct and indirect transitions and associated interventions, and then the path of combined transitions having the lowest combined weight is selected. The prediction model can additionally be constrained by permitting the selected path to pass through only certain predetermined allowable valence-arousal coordinates.

FIG. 1 shows an example of a path of combined transitions having the lowest combined weight. The lowest weight path is a three-arm transition from the initial state (sad) through a first intermediary state (anxious), through a second intermediary state (happy) and to the target state (optimistic). The first transition is achieved with the intervention of meditation and is assigned a weight of 80. The second transition is achieved with the intervention of journaling and is assigned a weight of 10. And the third transition is achieved with the intervention of improved sleep and is assigned a weight of 10. An alternate path of five transitions that also passes through the intermediary state "enthusiastic" has a higher combined weight.

The novel method uses a transition prediction model that predicts the expected efficacy of an intervention and the expected engagement by the user in that intervention. The method then determines the path of transitions having the lowest combined weight achievable using a set of available interventions.

The main stages of the method involve (1) capturing the input parameters, (2) determining the user's desired emotional state, (3) preparing the parameters for the predictive model, (4) querying the predictive model and computing the weights of each transition, (5) determining the path of transitions having the smallest combined weight and thus the greatest likelihood of achieving the desired state, and (6) recommending to the user the successive interventions associated with the path of transitions.

Figure 2:
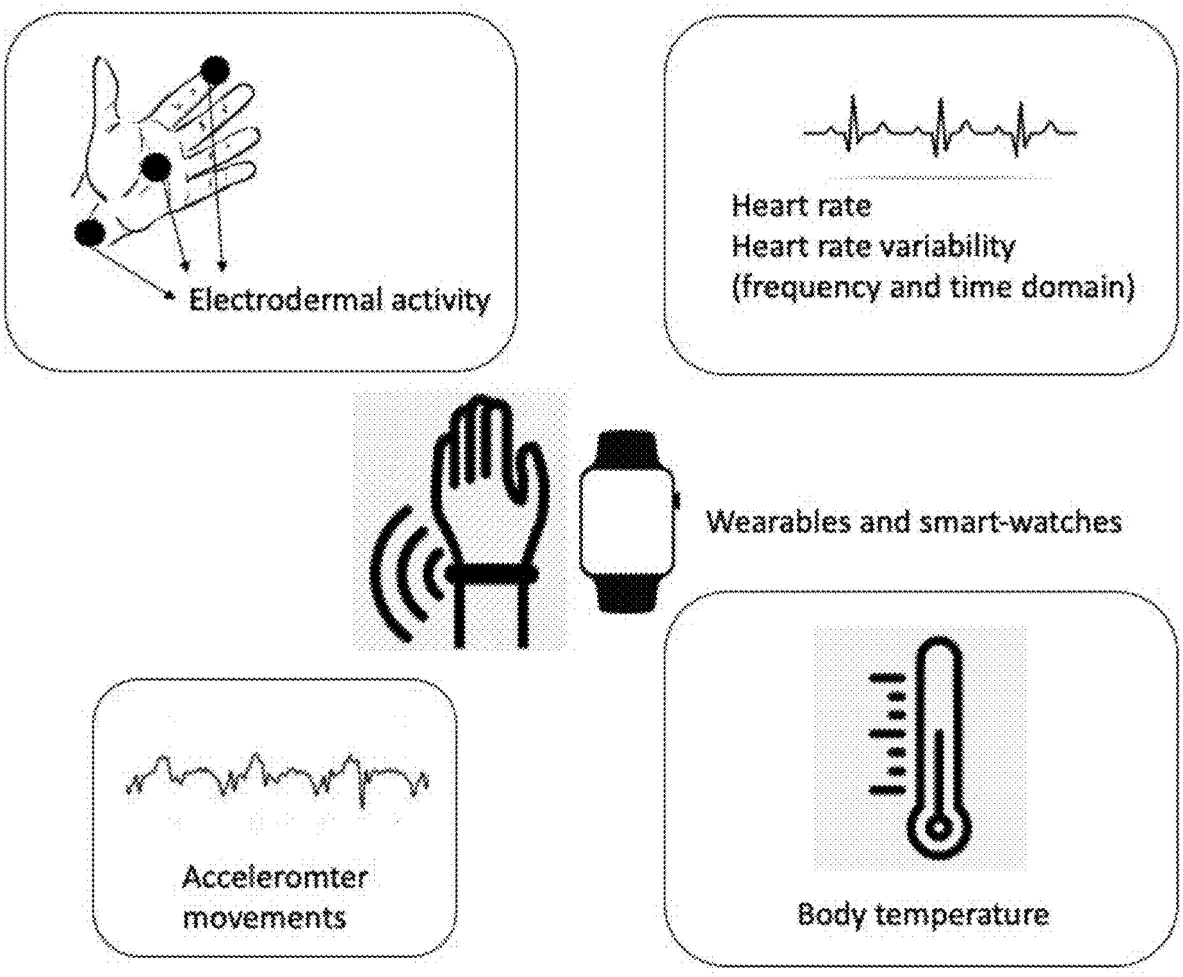
FIG. 2 illustrates types of sensor measurements used by the smartphone app.

The first stage of the method involves capturing the input parameters. The user's initial emotional state can be captured automatically by using sensors that measure physiological and physical parameters. The conscious input of the user is not required. Because such parameters respond to changes in a person's emotional state, they provide a proxy for measuring emotional states. Sensor measurements used by the novel method include, but are not limited to, heart rate, heart rate variability in the frequency and time domain (HRV), electrodermal activity (EDA), EEG, body temperature and body movements. Off-the-shelf devices, such as fitness trackers, smart watches and wellness wearables typically measure one or more of the aforementioned signals, which are illustrated in FIG. 2. Physiological parameters of the user are also used by the novel method for purposes other than to determine the user's initial emotional state, such as to match the user to similar prior users who have engaged in the same interventions.

In one embodiment, the user directly reports the user's initial state using various self-reporting icons, sliders and scales displayed by the mobile app on the screen of the user's smartphone. For example, the user can select an emotional state shown on the screen, such as "sad", "happy", "tense", "excited", "calm", etc. Alternatively, the user can use a sliding scale to select the degree that the user is currently feeling each of four emotions "happy", "sad", "angry" and "afraid". For example, each of these emotions can be rated 1-5 using a slider on the screen.

The novel method also uses the user's personal characteristics to match the user to similar prior users who have engaged in the same interventions. Thus, the user's personal characteristics inform the transition prediction model. The transition prediction model uses personal characteristics such as age, gender, socio-economic status, employment status and personality qualities (Big 5). The user of the mobile app can input the personal characteristics through questionnaires displayed on the user's smartphone. Alternatively, the personal characteristics can be automatically captured by user modeling algorithms that rely on data obtained from the user's smartphone, such as web browsing history, Google tags and calendar events.

The second stage of the method involves determining the user's desired emotional state. Similarly to reporting the initial state, the user can also directly indicate the targeted emotional state that the user desires to achieve by using the novel mobile app. For example, the user can select the user's desired emotional state from options shown on the screen, such as "happy", "enthusiastic" and "optimistic". Alternatively, the desired emotional state is dictated by the particular wellbeing app. For example, a meditation app may pre-set the state "calm" as the default desired state, or a sleep app may pre-set the desired state as "relaxed". Or the person recommending use of the app, such as a coach, employer, clinician, therapist or psychologist) may pre-set the desired state for the user. For example, an employer recommending that its employees use a productivity app may pre-set the desired state to "focused".

The third stage of the method involves preparing the parameters for the predictive model. Each of the user's initial state and the user's desired state is input into the transition prediction model as a vector of two numbers (valence, arousal). Where states are detected automatically by physiological parameters, such as HRV and EDA, the emotional states are already described in terms of valence and arousal coordinates. Electrodermal activity (EDA) is conventionally associated with the degree of arousal, and heart rate variability (HRV) is conventionally associated with the degree of valence.

In implementations of the mobile app in which the user reports the initial state and the desired state as categorical variables such as "anxious", "sad", "tense", "happy", "relaxed", "focused", etc., each categorical variable is converted by the app into a numeric variable, such as the 2-number vector of valence and arousal. The categorical variables from which the user selects correspond to emotional states conventionally defined by psychological models, such as Profile of Mood States (POMS) and Positive and Negative Affect Schedule (PANAS). These psychological models map emotional and cognitive states into the valence-arousal coordinate system. For instance, the "calm" state corresponds to low arousal and high valence, the "angry" state corresponds to high arousal and low valence, and the "excited" state corresponds to high arousal and high valence.

The fourth stage of the method involves querying the predictive model and computing the weights of each transition. The transition prediction model used by the novel method is built by mapping the input parameters and the interventions available to the user to the likelihood of achieving the target state, as indicated by the predicted efficacy of the intervention and the user's predicted engagement with the intervention. Based on past experience with prior users, the model learns the weights of transitions from initial states to target states. The model can be structured as a machine learning model based on linear regression, an ensemble model, or a deep neural network model. The model learns from historical information about transitions achieved by specific users engaging in particular interventions contained in the database. The model learns the probable efficacy (e.g., improvement in user's wellbeing) and the probable engagement (e.g., completion rate) of interventions undertaken by prior users with specific known input parameters and achieved target states.

In an alternative embodiment, the model predicts the engagement level and the efficacy level each intervention based on the prior engagement of the user with the intervention and on the prior efficacy of the intervention undertaken by the user in past experiences with the intervention. The predicted engagement and efficacy is not based on the past experience of other users in the alternative embodiment.

The probable (or predicted) efficacy and engagement are converted into weights that are inversely proportional to the efficacy likelihood and the engagement likelihood. The novel method uses the inverse proportion of the likelihood of being efficacious and the likelihood that the user will engage with the intervention in order to allow the use of graph theory tools for computing the shortest path between the initial states and the targeted states. In alternative embodiments, however, the method uses weights that are directly (rather than inversely) representative of the likelihoods of engagement and efficacy. The total weight of a transition is the sum of the weight for efficacy and the weight for engagement. The transition prediction model is queried for all available interventions 1 to n, and each transition achieved by an intervention is assigned a corresponding weight w1, w2, . . . wn. Thus, the prediction model determines the likely end state achievable by each intervention, as well as the weight of the transition to that end state.

In one implementation, the valence and arousal position of each intermediary state actually reached in a transition by the current user is measured and compared to the predicted target state of that transition. If the predicted target state and the measured intermediary state differ, then the measured state achieved by the intervention under particular parameters is stored in the database in order to improve future predictions of the model.

The fifth stage of the method involves determining the path of transitions having the smallest combined weight and thus the greatest likelihood of achieving the desired state. The desired emotional state can seldom be achieved from the initial state by undertaking a single intervention, so a single transition to the desired state typically does not have the smallest weight from among all possible paths of transitions to the desired state.

The combined weights of 2-transition paths are also calculated to determine the path with the smallest combined weight. For each 2-transition path, the weight of the second transition is predicted by taking the end state after the first transition as the initial state for the second transition. The predictive model calculates the weights of n×n 2-transition paths, where n is the number of available interventions. Each of n×n 2-transition paths is assigned the combined weight that is the sum of the predicted weights of the first and second transitions. The combined weights of paths with three or more transitions are also calculated to determine the path with the smallest combined weight. Again, the combined weight is the sum of the predicted weights of all of the transitions.

The sixth stage of the method involves recommending to the user the successive interventions associated with the path of transitions that has the smallest weight and therefore the greatest likelihood of achieving the user's desired emotional state. For example, the mobile app prompts the user to engage in the first intervention and then to engage in the second intervention of the 2-transition path having the greatest likelihood of achieving the user's desired state from among all possible paths of transitions. The user is prompted to engage in the inventions via the smartphone screen or by an audio prompt.

Figure 3:
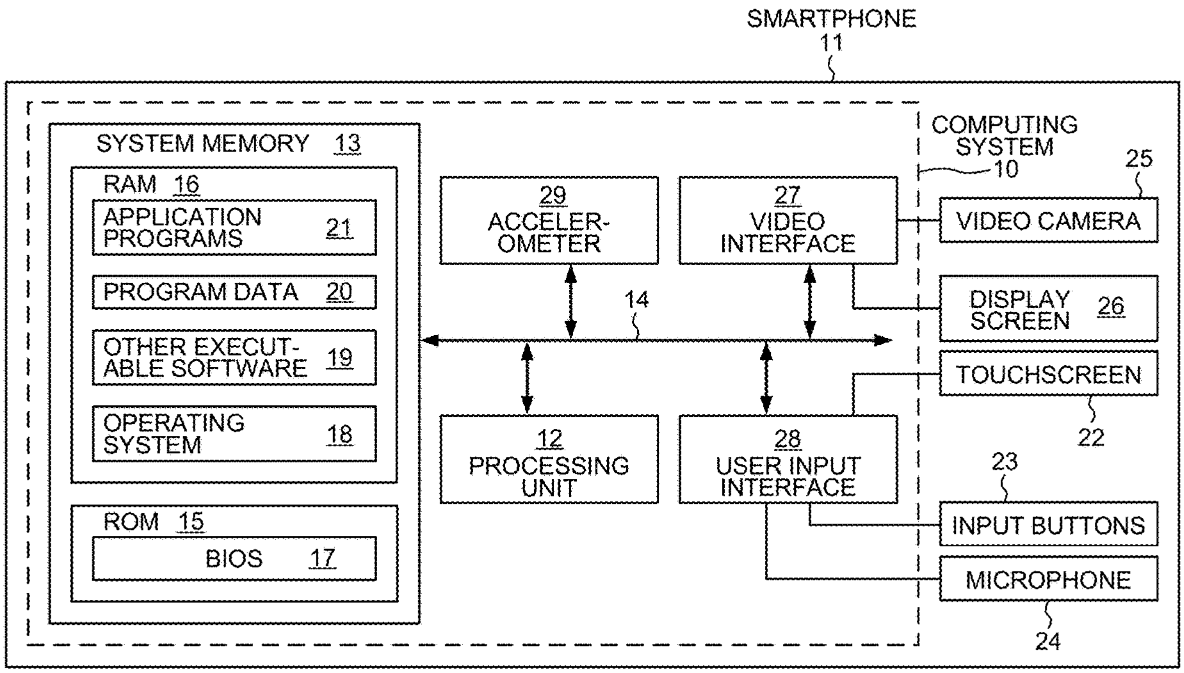
FIG. 3 is a schematic diagram of a computing system that runs the smartphone app for delivering immediate wellbeing interventions.

FIG. 3 is a simplified schematic diagram of a computing system 10 on a smartphone 11, which is a mobile telecommunications device. System 10 can be used to implement a method for delivering immediate wellbeing interventions having a greater likelihood of achieving the user's desired emotional or cognitive state. Portions of the computing system 10 are implemented as software executing as a mobile App on the smartphone 11. Components of the computing system 10 include, but are not limited to, a processing unit 12, a system memory 13, and a system bus 14 that couples the various system components including the system memory 13 to the processing unit 12. Computing system 10 also includes computing machine-readable media used for storing computer readable instructions, data structures, other executable software and other data.

The system memory 13 includes computer storage media such as read only memory (ROM) 15 and random access memory (RAM) 16. A basic input/output system 17 (BIOS), containing the basic routines that transfer information between elements of computing system 10, is stored in ROM 15. RAM 16 contains software that is immediately accessible to processing unit 12. RAM includes portions of the operating system 18, other executable software 19, and program data 20. Application programs 21, including smartphone "apps", are also stored in RAM 16. Computing system 10 employs standardized interfaces through which different system components communicate. In particular, communication between apps and other software is accomplished through application programming interfaces (APIs), which define the conventions and protocols for initiating and servicing function calls.

Information and user commands are entered into computing system 10 through input devices such as a touchscreen 22, input buttons 23, a microphone 24 and a video camera 25. A display screen 26, which is physically combined with touchscreen 22, is connected via a video interface 27 to the system bus 14. Touchscreen 22 includes a contact intensity sensor, such as a piezoelectric force sensor, a capacitive force sensor, an electrodermal activity (EDA) sensor, an electric force sensor or an optical force sensor. These input devices are connected to the processing unit 12 through video interface 27 or a user input interface 28 that is coupled to the system bus 14. For example, user input interface 28 detects the contact of a finger of the user with touchscreen 22 or the electrodermal activity of the user's skin on a sensor. In addition, other similar sensors and input devices that are present on wearable devices, such as a smartwatch, are connected through a wireless interface to the user input interface 28. One example of such a wireless interface is Bluetooth. The wireless communication modules of smartphone 10 used to communicate with wearable devices and with base stations of a telecommunications network have been omitted from this description for brevity. Computing system 10 also includes an accelerometer 29, whose output is connected to the system bus 14. Accelerometer 29 outputs motion data points indicative of the movement of smartphone 11.

Figure 4:
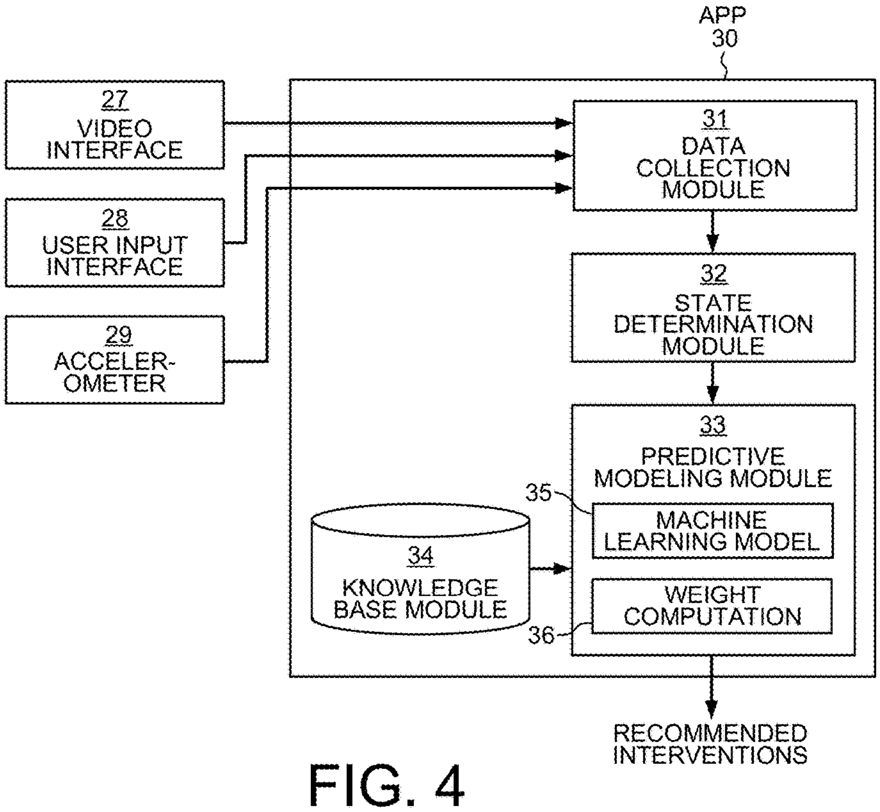
FIG. 4 is a schematic diagram of the components of the smartphone app that recommends interventions most likely to transition the user to a desired emotional state.

FIG. 4 is a schematic diagram of the components of one of the application programs 21 running on smartphone 11. This mobile application (app) 30 is part of computing system 10. App 30 is used to implement the novel method for delivering immediate wellbeing interventions having a greater likelihood of achieving the user's desired emotional or cognitive state. App 30 includes a data collection module 31, a state determination module 32, a predictive modeling module 33 and a knowledge base module 34. In one embodiment, mobile app 30 is one of the application programs 21. In another embodiment, at least some of the functionality of app 30 is implemented as part of the operating system 18 itself. For example, the functionality can be integrated into the iOS mobile operating system or the Android mobile operating system.

Data collection module 31 collects data representing user interactions with smartphone 11, such as touch data, motion data, video data and user-entered data. For example, the touch data can contain information on electrodermal activity (EDA) of the user, and the motion data or video data can be used to derive information on heart rate variability (HRV). FIG. 4 shows that data collection module 31 collects data from video interface 27, user input interface 28 and accelerometer 29. In addition, data collection module 31 also collects reports in which users indicate their perceived physiological, emotional and cognitive states.

Figure 5:
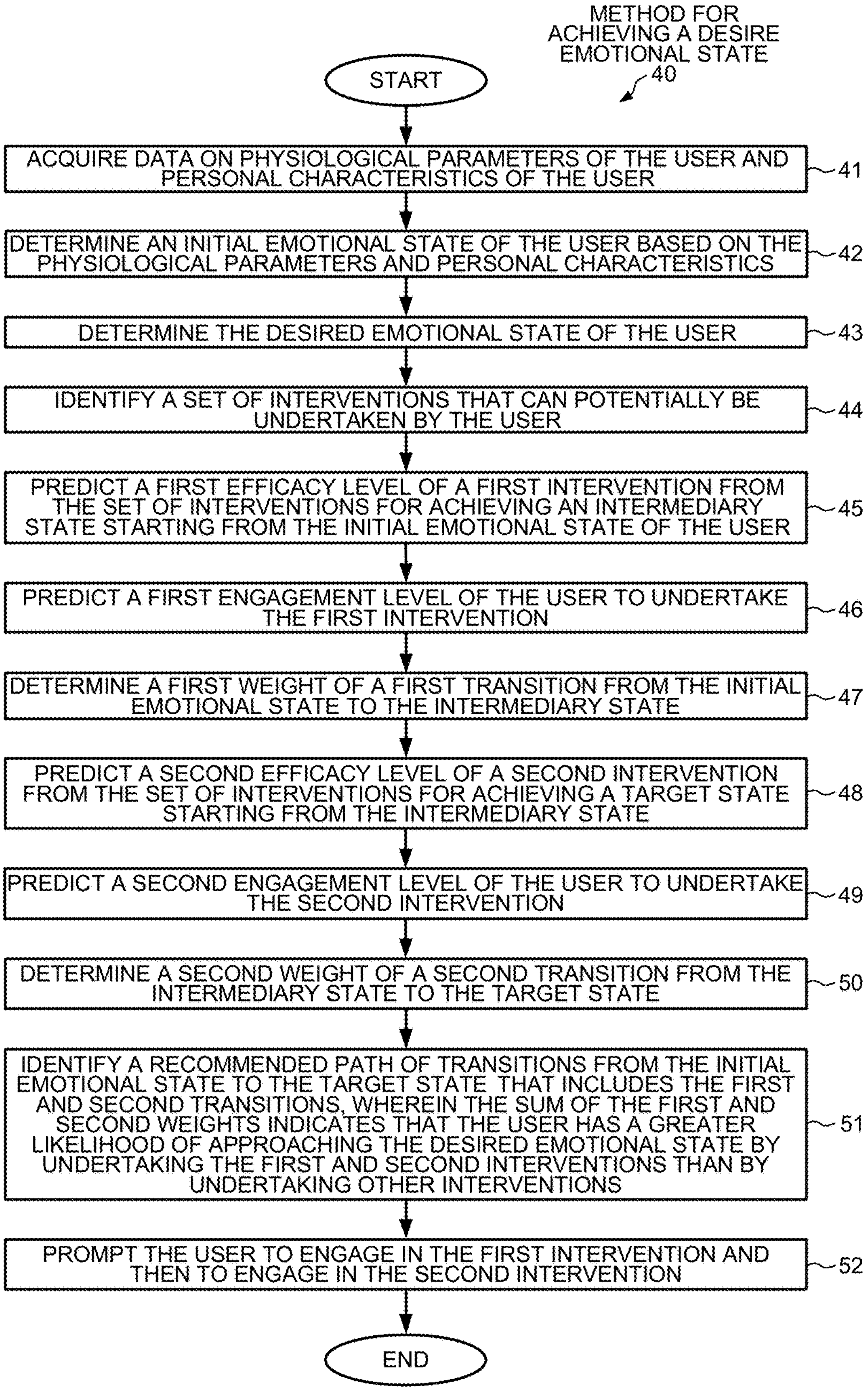
FIG. 5 is a flowchart of steps of a method by which the smartphone app determines the interventions most likely to transition the user to the desired emotional state.

FIG. 5 is a flowchart of steps 41-52 of a method 40 by which App 30 uses sensed data acquired via smartphone 11, personal characteristics entered by the user, and knowledge of the success of various interventions with prior users to prompt the user to engage in those selected interventions that are most likely to transition the user from the user's initial emotional or cognitive state to the user's desired state. In this embodiment, App 30 is a mindfulness app that guides the user to achieve a desired emotional or cognitive state (hereinafter an emotional state) of relaxation, calm, focus, contentment or sleepiness. The steps of FIG. 5 are described in relation to computing system 10 and App 30 which implement method 40.

In step 41, system 10 is used to acquire data concerning physiological parameters of the user and personal characteristics of the user. Step 41 is performed using data collection module 31 of App 30. In this embodiment, system 10 acquires data concerning two physiological parameters of the user. The user is wearing a smartwatch or fitness tracker wristband with sensors that acquire data from which App 30 calculates the user's average heart rate variability (HRV) and electrodermal activity (EDA). In other embodiments, the user's body temperature and the accelerometer movements of smartphone 11 are also acquired in step 41. In this example, datapoints relating to the user's heart rate are captured every 20 milliseconds from which the average HRV is calculated. The data relating to heart rate was captured by the smartwatch and computed by App 30 to result in an average heart rate variability AVG(HRV) of 45. Datapoints relating to the user's EDA are captured at a rate of 25 per minute. The data relating to electrodermal activity was captured by the smartwatch and computed by App 30 to result in an average electrodermal activity variability AVG (EDA) of 17.

The user's personal characteristics are static or semi-static, and are entered by the user into App 30 in the onboarding phase of the app. In this example, App 30 uses three personal characteristics: age, gender and personality. The user's age is 49, and the user's gender is male. In the input data, male is designated as "0", and female is designated at "1". In this example, personality is self-reported by the user using the Big-5 Model, which includes openness (O), conscientiousness (C), extraversion (E), agreeableness (A), and neuroticism (N). In this example, the user has self-reported his personality as O=47, C=23, E=44, A=30 and N=43.

In step 42, the initial emotional state of the user of App 30 is determined. Step 42 is performed using state determination module 32 of App 30. In this embodiment, system 10 determines the user's initial emotional state based on the two physiological proxy signals HRV and EDA. In other embodiments, system 10 determines the user's initial emotional state based on physiological signals and on the information concerning the user's personal characteristics entered by the user, such as age, gender and personality.

Conventional psychological models, such as Profile of Mood States (POMS) and Positive and Negative Affect Schedule (PANAS), place emotional and cognitive states in a valence-arousal coordinate system. For example, a valence value can be plotted along the abscissa, and an arousal value can be plotted along the ordinate. Thus, emotional states are mapped to numerical values (valence, arousal). For instance, happy, optimistic and enthusiastic states correspond to high valence and high arousal. Calm and relaxed states correspond to high valence and low arousal. Angry, anxious and stressed states correspond to low valence and high arousal. And sad states correspond to low valence and low arousal.

The user's initial emotional state can be directly reported by the user in a subjective manner by selecting a textual description of the state, such as happy, optimistic, enthusiastic, calm, relaxed, angry, anxious, afraid, stressed or sad. Alternatively, sliders can be displayed on the touchscreen 22 of smartphone 11 that allow the user to select the degree to which the user is feeling each of the four states: happy (high valence, high arousal), relaxed (high valence, low arousal), anxious (low valence, high arousal) and sad (low valence, low arousal).

However, in this embodiment, the user's initial emotional state is captured by computing system 10 without the conscious input of the user. The method 40 uses heart rate variability (HRV) as an indication of the user's valence, and electrodermal activity (EDA) as an indication of the user's arousal. Thus, in step 42, the user's initial emotional state is determined based on the physiological parameters HRV and EDA as sensed by computing system 10.

Figure 6:
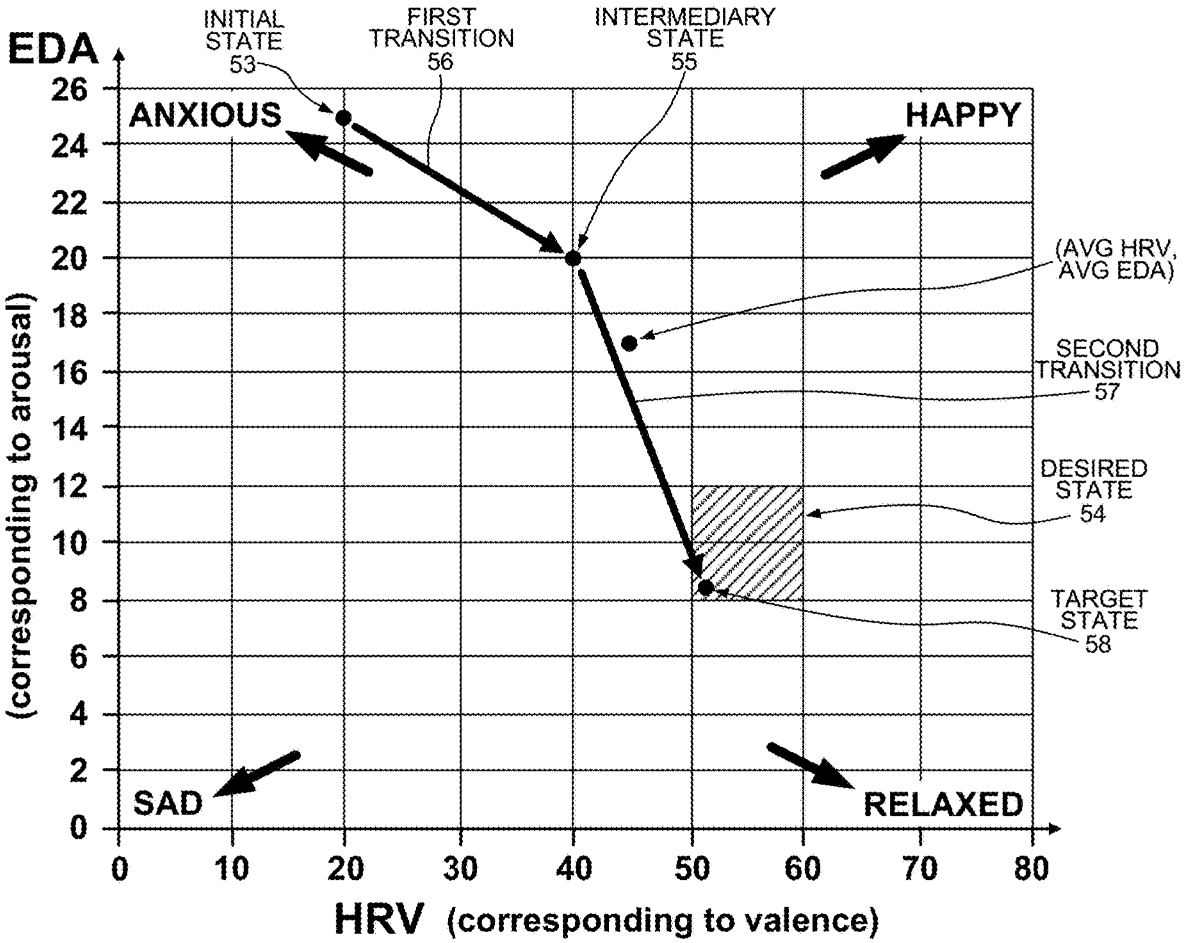
FIG. 6 is a diagram of emotional states plotted in a coordinate system of HRV/valence along the abscissa and EDA/arousal along the ordinate.

FIG. 6 is a diagram illustrating various emotional states mapped in an HRV-EDA coordinate system, with valence plotted along the abscissa and arousal plotted along the ordinate. The four emotional states happy, relaxed, anxious and sad are shown in the four corners of the mapped area. The user's initial emotional state 53 is plotted in FIG. 6 at HRV=20 and average EDA=25. The physiological parameters of the user's average HRV=45 and average EDA=17 are also plotted in FIG. 6.

In step 43, the user's desired emotional state is determined. Step 43 is performed using state determination module 32 of App 30. In one embodiment, the user is shown the user's initial state in a valence-arousal coordinate system and allowed to shift the position to that of a desired state—usually to the right in the emotional state space of FIG. 6. The corresponding HRV-EDA coordinates of the desired state are then used at the goal to be achieved by the immediate interventions.

In this embodiment, however, the user selects a desired emotional state from a list of states to be achieved by engaging with the interventions recommended by App 30. In this example, the user has selected a "focused" state. App 30 determines that a "focused" state corresponds to an area in the emotional state space having the target parameters of HRV in a range 50-60 and EDA in a range 8-12. FIG. 6 shows the area of the desired emotional state 54 mapped in the HRV-EDA coordinate system. Thus, the goal of the immediate interventions is to transition the user from the initial emotional state 53 to the desired emotional state 54.

In step 44, a set of interventions that can potentially be undertaken by the user is identified. Step 44 is performed using predictive modeling module 33 and knowledge base module 34. A database of the knowledge base module 34 is used to build a model for predicting the efficacy and the engagement of each intervention in the identified set of interventions that are available to the user. The database stores historical information on parameters related to how the available interventions were applied to other prior users of App 30. A particular intervention is identified as potentially to be undertaken only if historical information is available from which to predict the efficacy and engagement if undertaken by the particular user.

FIG. 7 shows three exemplary entries in a database indicating how three particular interventions were undertaken by particular prior users of App 30. Each intervention is denoted by an 8-vector intervention variable (one-hot encoding). Thus, there are eight possible interventions in this example. The one-hot encoding is used with machine learning instead of a categorical variable for each specific intervention. For example, (1,0,0,0,0,0,0,0) corresponds to a first intervention, such as guided meditation to improve focus and feel more relaxed, (0,1,0,0,0,0,0,0) corresponds to a second intervention, such as listening to a guided narrative to feel more focused, (0,0,1,0,0,0,0,0) corresponds to a third intervention, such as undertaking an exposure exercise, (0,0,0,1,0,0,0,0) corresponds to a fourth intervention, such as keeping a journal or diary, etc.

For each user who undertook an intervention in the past, the database contains the personal characteristics of the user, such as age, gender and personality. The personality is denoted in the database as a 5-ventor variable corresponding to the BIG-5 traits. For the first entry in the database, for example, the prior user exhibited openness of O=34, conscientiousness of C=49, extraversion of E=23, agreeableness of A=33, and neuroticism N=44. The database also includes the physiological parameters of the prior uses, in this case the average HRV and average EDA of each user who undertook an intervention. In one example, the average HRV and EDA information is averaged over a week.

The database includes the start HRV and the start EDA corresponding to the immediate measurements at the time each prior user started a specific intervention by beginning an app session. The ending HRV and ending EDA immediately after each prior user stopped engaging in an intervention is also stored in the knowledge base module 34.

Finally, the database also includes the efficacy of each prior intervention and the prior user's engagement with that intervention. The efficacy is denoted as a value between 0 and 1 that corresponds to how effective the intervention was at transitioning the prior user to the prior user's desired emotional state as defined by HRV and EDA coordinates. Thus, the efficacy value is a comparison of the targeted HRV and EDA to the HRV and EDA values actually achieved through the intervention. For example, a 0.93 efficacy signifies that in the HRV-EDA coordinate system, the desired transition to the targeted HRV and EDA values was 93% achieved.

The engagement is denoted as a value between 0 and 1 that corresponds to how well the prior user adhered to the intervention program. For example, if the intervention is listening to a guided narrative (an audio tape), then the engagement is the percentage of the audio tape that the user listened to. If the duration of the audio narrative was four minutes, and the user listened to only three minutes before stopping, then the engagement is 0.75, meaning that 75% of the audio tape was listened to.

In step 45, intermediary states are predicted that are achievable by the user by engaging in each of the available interventions in the identified set of interventions. The achievable intermediary states are predicted by predicting the efficacy and engagement of the user with each intervention. In step 45, the computing system 10 begins by predicting a first efficacy level of a first intervention from the set of interventions for achieving an intermediary state 55 starting from the initial emotional state of the user determined in step 42. The computing system 10 predicts the efficacy using a predictive model based on machine learning that maps the parameters of age, gender, personality, average HRV, average EDA, start HRV, start EDA and the selected intervention to the predicted efficacy. The model is trained using the information relating to the prior users that is stored in the knowledge base module 34. Parameters for each of the features are calculated by machine learning on the knowledge base of features, including efficacy and engagement, acquired from interventions undertaken by prior users.

In step 46, achievable intermediary states are predicted for the available interventions by predicting the engagement of the user with each intervention. The outcomes of all available interventions in terms of efficacy and engagement are predicted starting from the initial state of the user as a function of the user's personal characteristics and physiological parameters, in this case f(age=49, gender=0, personality=(47,23,44,30,43), average HRV=45, average EDA=17, start HRV=20 and start EDA=25). In this example, the machine learning model 35 of the predictive modeling module 33 predicts eight expected efficacy and engagement values, and thereby derives the likely end HRV and end EDA of each of the achievable intermediary states for the eight available interventions (1,0,0,0,0,0,0,0), (0,1,0,0,0,0,0,0), (0,0,1,0,0,0,0,0), (0,0,0,1,0,0,0,0), (0,0,0,0,1,0,0,0), (0,0,0,0,0,1,0,0), (0,0,0,0,0,0,1,0) and (0,0,0,0,0,0,0,1).

In step 46, the computing system 10 begins by predicting a first engagement level of the first intervention of the set of interventions. For the first intervention, the efficacy and engagement are predicted based on the function f(age=49, gender=0, personality=(47,23,44,30,43), AVG HRV=45, AVG EDA=17, start HRV=20, start EDA=25, INTERVENTION=(1,0,0,0,0,0,0,0)). In this example, the predicted efficacy is 0.56, and the predicted engagement is 0.25, which means that the user will engage in only 25% of the intervention (e.g., listen to only 25% of the audio tape) and will transition only 14% of the way to the desired state (i.e., reach end HRV=40 and end EDA=20 instead of the desired focused emotional state area HVR=50-60; EDA=8-12). For an engagement of 100%, the user transitions to an end state determined only by the predicted efficacy.

In step 47, a weight computation module 36 of the predictive modeling module 33 assigns weights to the transitions that are predicted to be achieved by each of the interventions based on the predicted efficacy and predicted engagement. In this embodiment, the weight of each transition is inversely proportional to the extent to which the transition reaches the desired state. For example, a transition that achieves 90% of the desired change of state would have a weight of 10%. Weights that are inversely proportional to predicted efficacy or probability of success are used so as to enable the use of graph theory tools for identifying those combined transitions from the initial state to the target state that have the highest likelihood of achieving the desired state.

In other embodiments, the weighting is performed inversely such that a larger weight is assigned to transitions that are more likely to achieve the desired state. In step 47, the computing system 10 begins by determining a first weight of a first transition 56 from the initial emotional state 53 to the intermediary state 55 (e.g., HRV=40, EDA=20), which was predicted to be achieved by the first intervention.

In this example, it is assumed that none of the interventions results in a predicted engagement and predicted efficacy that will transition the user all the way into the desired state, in this case the desired focused emotional state area 54 of HVR=50-60 and EDA=8-12.

In step 48, target states are predicted that are achievable by the user by engaging in each of the available interventions starting from the intermediary states predicted to be achieved by the first implemented interventions. Similarly as in step 45, the achievable target states are predicted by predicting the efficacy and engagement of the user for each intervention. In step 48, the computing system 10 begins by predicting a second efficacy level of a second intervention from the set of interventions that results in a second transition 57 from the intermediary state 55 (which is the starting state for step 48) to a target state 58. In this example, the intermediary state 55 predicted to be achieved by the first intervention was HRV=40 and EDA=20. Similarly as in step 45, the prediction is performed by machine learning model 35 trained by using the information relating to the prior users that is stored in the knowledge base module 34.

In step 49, the achievable target state is predicted for each intervention by predicting the engagement of the user with that intervention. The outcomes of all available interventions in terms of efficacy and engagement are predicted from the intermediary states predicted to be achieved by the first interventions. In step 49, the computing system 10 begins by predicting a second engagement level of the second intervention for which the efficacy was predicted in step 48 and which begins at the intermediary state 55 predicted to be achieved by the first intervention.

Thus, in steps 48-49, the predictive model is queried again by using the intermediary state 55 predicted to be achieved by the first intervention as the starting state for each of the eight available interventions. The predicted target states for the eight available interventions are the end states reached by the combination of two transitions (forming two-arm transitions) resulting from two interventions. Steps 45-46 and 48-49 are repeated such that eight end states of two-arm transitions are determined for each of the eight available first interventions. Thus, steps 45-46 and 48-49 are repeated for the eight available interventions to predict the end states of sixty-four two-arm transitions.

In step 50, based on the predicted efficacy and engagement, weights are assigned to the second transitions that are predicted to be achieved by each of the interventions. The computing system 10 begins by determining a second weight of the second transition 57 from the intermediary state 55 (e.g., HRV=40, EDA=20) to the target state 58 predicted to be achieved by the second intervention. Thus, steps 47 and 50 are repeated for the sixty-four two-arm transitions and generate sixty-four pairs of weights.

In some embodiments, the predictive model can be queried for three consecutive interventions in order to generate weights for each of the resulting three-arm transitions. However, in this embodiment, the number of consecutive interventions to be undertaken by the user is limited to two. This limits the number of calculations that the computing system 10 must perform to weight the many possible transitions.

In step 51, app 30 identifies a recommended path of transitions from the initial emotional state of the target state that includes the first transition and the second transition where the sum of the first weight and the second weight indicates that the user has a greater likelihood of approaching the desired emotional state by undertaking the first intervention and the second intervention than by undertaking other combinations of interventions. App 30 identifies the two transitions of the path that have the smallest combined weight, which indicates that the user has the greatest likelihood of approaching the user's desired emotional state by undertaking the two interventions associated with the two transitions. In the example of FIG. 6, the path of transitions 56-57 not only approaches the desired emotional state 54, but the target state 58 achieved by the second transition 57 also falls within the area HVR=50-60 and EDA=8-12 of the desired emotional state "focused".

In step 52, app 30 prompts the user to engage in the first intervention and then to engage in the second intervention in order to achieve the user's desired emotional state. The user is prompted on the display screen 26.

Another implementation of App 30 is described below. In this implementation, App 30 performs six steps: (1) capturing input parameters, (2) determining the user's desired emotional state, (3) preparing the parameters for the predictive modeling module, (4) querying the predictive module and computing the weights of each transition, (5) determining the path of transitions having the smallest combined weight and thus the greatest likelihood of achieving the desired state, and (6) recommending the interventions associated with the path of transitions to the user.

In the first step of capturing the input parameters, the user's initial emotional state is measured by an electronic device (e.g., a mobile phone) as valence and arousal coordinates. In addition, the user's personal characteristics (e.g., gender,) and other characteristics (e.g., user's perceived stress level) are captured by other digital mental health applications and then incorporated into App 30. The user's initial state and personal characteristics are input into the transition prediction model and are used to train the model together with data from past users of App 30 and other applications designed to increase subjective well-being.

In the second step, the user's desired emotional state is determined.

In the third step, the predictive model is prepared using the gathered parameters. For each possible transition, the predictive model identifies the intervention that produced the transition, indicates the target emotional state that the user can likely achieve and calculates the weight of the transition based on the predicted efficacy and engagement of the intervention the produced the transition. For example, possible interventions include journaling, meditation and positive psychology. The inputs to the model include the user's initial state, the user's gender and the user's Big-5 personality score.

In this example, the user's initial state is "sad", which is defined as a valence of −0.7 and an arousal of −0.1 in a valence-arousal coordinate system of −1 to +1 for both valence and arousal coordinates. The user's desired state is "happy", which is defined as a valence of 0.6 and an arousal of 0.1. The user is male. The Big-5 personality qualities of the user are: openness 10, conscientiousness 20, extraversion 20, agreeableness 70 and neuroticism 60, all of which measured on a scale of 0 to 100. The user has a subjective wellbeing of 50, measured on a scale of 0 to 100. These parameters are input into the predictive model, which is a linear regression decision tree model. For each available intervention, the model outputs the predicted valence and arousal that will be achieved by the intervention. For example, a journaling intervention is predicted to result in a predicted valence of −0.3 and a predicted arousal of −0.1 for the particular user.

In the fourth step, the predictive model is queried, and the weights of each transition are computed. In this step, for each available intervention, the model receives as input the identity of an available intervention and the end valence and end arousal predicted to be achieved by that intervention. If the desired emotional state is not reached by a first transition, then the model determines the valence and arousal predicted to be achieved by an additional intervention using the end state of the first transition as the starting state of a second transition achieved by the additional intervention. Thus, the model calculates the end states of two-arm transitions. For n available interventions, the model calculates n×n end states of two-arm transitions.

In the fifth step, the model determines the weight of each transition based on the predicted efficacy of the intervention that produced the transition for the particular user and on the predicted engagement that the particular user is predicted to demonstrate for that intervention. For the end states of the n×n two-arm transitions that approach the desired emotional state to within a predetermined margin of error (e.g., +/−0.1 valence and/or arousal), the model adds the weights of both transition arms to determine the combined weight of each two-arm transition. Still in the fifth step, the model determines the path of transitions having the smallest combined weight and thus the greatest likelihood of approaching the desired state to within the predetermined margin of error.

In the sixth step, App 30 recommends to the user the successive interventions associated with the path of transitions that has the greatest likelihood of approaching the desired state. In one example, the path of transitions with the greatest likelihood of achieving the desired emotional state includes a first transition associated with a meditation intervention and a second transition associated with a journaling intervention. In this example, the combined weight of these two transitions is 30 (20 for first transition and 10 for second transition), which is smaller than the combined weight of every other two-arm transition and smaller than the weight of every single transition that achieves an end state within the predetermined margin of error from the desired emotional state.

Although the present invention has been described in connection with certain specific embodiments for instructional purposes, the present invention is not limited thereto. Accordingly, various modifications, adaptations, and combinations of various features of the described embodiments can be practiced without departing from the scope of the invention as set forth in the claims.

What is claimed is:

1. A method for achieving a desired emotional state of a user, the method comprising:

obtaining a machine learning model trained to determine respective weights of transitions in a multi-dimensional coordinate space between respective pairs of emotional states, based on historical information about respective transitions achieved by prior persons between respective pairs of emotional states, each respective pair of emotional states including an initial state and a target state, each respective transition to be achieved by a respective person via an intervention from among a set of interventions, and each respective weight corresponding to an expected success in achieving the target state as determined at least by determining (i) a likelihood that the respective person is to engage in the intervention, and (ii) a likelihood that the intervention, when engaged in, is to induce the target state, executing a data collection module designed to acquire data concerning physiological parameters of the user and personal characteristics of the user, the physiological parameters collected by one or more sensors on a user device configured to automatically monitor the physiological parameters of the user and the personal characteristics of the user collected by the user device;

determining an initial emotional state of the user based on the physiological parameters and personal characteristics, the initial emotional state defined by a first set of coordinates in the multi-dimensional coordinate space;

determining the desired emotional state of the user, the desired emotional state collected by the user device, the desired emotional state defined by a second set of coordinates in the multi-dimensional coordinate space;

providing to the machine learning model as inputs (i) the initial emotional state of the user, and (ii) the desired emotional state of the user;

via the trained machine learning model, based on the inputs:

identifying a plurality of intervention sequences capable of being undertaken by the user to transition in the multi-dimensional coordinate space from the initial emotional state to within a margin of error of the desired emotional state, each of the plurality of intervention sequences including a respective set of two or more different interventions from among the set of interventions;

for each intervention sequence from among the plurality of intervention sequences:

predicting a first weight of a first transition in the multi-dimensional coordinate space to be achieved via a first intervention from the respective set of two or more interventions, the first intervention transitioning the user from the initial emotional state to one of one or more intermediary states, and the first weight being based on a predicted efficacy level of the first intervention and a predicted engagement level of the user in undertaking the first intervention;

predicting a second weight of a second transition to be achieved via a second intervention from the respective set of two or more interventions, the second intervention transitioning the user in the multi-dimensional coordinate space from one of the one or more intermediary states to within the margin of error of the desired emotional state, and the second weight being based on a predicted efficacy level of the second intervention and a predicted engagement level of the user in undertaking the second intervention;

determining a combined predicted weight of the intervention sequence based at least on the first weight and the second weight, the combined predicted weight corresponding to an expected success of the user in transitioning in the multi-dimensional coordinate space from the initial emotional state to the desired emotional state by way of the intervention sequence, determining, from among corresponding combined predicted weights determined for each of the plurality of intervention sequences, a particular intervention sequence having a combined predicted weight indicative of a highest expectation of success of the user transitioning in the multi-dimensional coordinate space from the initial emotional state to the desired emotional state;

responsive to determining the particular intervention sequence, prompting the user, by display at the user device, to engage in the particular intervention sequence;

determining a measured emotional state of the user upon the user engaging in a particular intervention from among the particular intervention sequence; and updating the trained machine learning model based on the measured emotional state.

2. The method of claim 1, wherein the initial emotional state of the user is defined by a valence coordinate and an arousal coordinate in the multi-dimensional coordinate space.

3. The method of claim 2, wherein the initial emotional state of the user is determined by measuring a heart rate variability (HRV) and an electrodermal activity (EDA) of the user, wherein the initial emotional state of the user is defined by an HRV value and an EDA value, and wherein the HRV value represents the valence coordinate and the EDA value represents the arousal coordinate.

4. The method of claim 3, wherein the HRV and the EDA are measured by the one or more sensors and wherein the user device is a mobile electronic device.

5. The method of claim 4, wherein the mobile electronic device is a smartwatch, and wherein the initial emotional state is computed by a mobile app running on a smartphone.

6. The method of claim 1, wherein the personal characteristics of the user are selected from the group consisting of: age, gender, socio-economic status, employment status, openness, conscientiousness, extraversion, agreeableness, and neuroticism.

7. The method of claim 1, wherein the first intervention is selected from a group consisting of: writing down thoughts in a diary, engaging in guided meditation, listening to a guided audio narrative, watching an educational video, taking a nap, and exposing oneself to an anxiety trigger.

8. The method of claim 1, wherein the multi-dimensional coordinate space is defined by a valence coordinate and an arousal coordinate, wherein positions in the multi-dimensional coordinate space defined by greater valence coordinates and greater arousal coordinates correspond to optimistic emotional states, wherein positions in the multi-dimensional coordinate space defined by greater valence coordinates and lesser arousal coordinates correspond to calm emotional states, wherein positions in the multi-dimensional coordinate space defined by lesser valence coordinates and lesser arousal coordinates correspond to sad emotional states, and wherein positions in the multi-dimensional coordinate space defined by lesser valence coordinates and greater arousal coordinates correspond to anxious emotional states.

9. The method of claim 1, wherein the desired emotional state of the user is a more focused emotional state than the initial emotional state of the user.

10. The method of claim 1, wherein the multi-dimensional coordinate space is a coordinate space defined by two dimensions comprising emotional valence and emotional arousal.

11. The method of claim 1, further comprising training the machine learning model to determine the respective weights of the transitions between the respective pairs of emotional states in the multi-dimensional coordinate space based on the historical information.

12. The method of claim 1, wherein determining the desired emotional state includes:

causing the user device to display a graphical representation of the multi-dimensional coordinate space; and obtaining an indication of the desired emotional state via a user interaction in the graphical representation of the multi-dimensional coordinate space.

13. The method of claim 12, wherein the displayed graphical representation of the multi-dimensional coordinate space includes a graphical indication of the initial emotional state, the graphical indication of the initial emotional state being positioned at a first position in the graphical representation based on the first set of coordinates in the multi-dimensional coordinate space, and wherein obtaining the indication of the desired emotional state includes:

obtaining the user interaction, wherein the user interaction comprises a shift from the first position to a second position in the graphical representation of the multi-dimensional coordinate space, identifying a second set of coordinates in the multi-dimensional coordinate space, the second set of coordinates being based on the second position, and determining the desired emotional state based on the second set of coordinates.

14. The method of claim 1, wherein the one or more intermediary states consist of one intermediary state, wherein the first intervention is to transition the user from the initial emotional state to the one intermediary state, and wherein the second transition is to transition the user from the one intermediary state to the desired emotional state.

15. The method of claim 1, wherein updating the trained machine learning model based on the measured emotional state comprises further comprising:

comparing the measured emotional state to a predicted target state predicted by the training machine learning model to be achieved via the particular intervention, to identify a difference between the measured emotional state and the predicted target state; and providing an indication of the difference to the trained machine learning model to update the trained machine learning model based on the difference.

16. The method of claim 1, wherein the predicting of the first weight and the predicting of the second weight are further based on at least one of (i) identifying transitions in the multi-dimensional coordinate space achieved by persons with personal characteristics similar to the personal characteristics of the user, or (ii) identifying transitions in the multi-dimensional coordinate space achieved by persons with physiological parameters similar to the physiological parameters of the user.

* * * * *